United States Patent [19]
Schmidt et al.

[11] Patent Number: 5,712,168
[45] Date of Patent: Jan. 27, 1998

[54] METHOD FOR EVALUATING, MONITORING OR CONTROLLING THE EFFICIENCY, STABILITY, OR EXHAUSTION OF A COMPLEXING OR CHELATING AGENT PRESENT IN A CHEMICAL SOLUTION USED FOR OXIDIZING, DISSOLVING, ETCHING OR STRIPPING A SEMICONDUCTOR WAFER

[75] Inventors: Harald Okorn Schmidt, Leuven; Martien Johanna Maria Godelieve Bernard Baeyens, Oostende; Marc Marcel Annie Maria Heyns, Linden; Paul Mertens, Liedekerke, all of Belgium

[73] Assignee: IMEC, Leuven, Belgium

[21] Appl. No.: 384,272

[22] Filed: Feb. 3, 1995

[51] Int. Cl.$^6$ .................................................. G01N 7/00
[52] U.S. Cl. .................. 436/135; 436/34; 436/129; 436/148
[58] Field of Search ................... 436/135, 148, 436/34, 129

[56] References Cited

U.S. PATENT DOCUMENTS

| | | | |
|---|---|---|---|
| 2,617,940 | 11/1952 | Giguere | 436/135 |
| 5,081,045 | 1/1992 | McGill | 436/135 |
| 5,100,624 | 3/1992 | Dougherty | 422/68.1 |
| 5,290,361 | 3/1994 | Hayashida et al. | 134/2 |
| 5,302,311 | 4/1994 | Sugihara et al. | 252/102 |
| 5,438,002 | 8/1995 | Varende et al. | 436/129 |
| 5,474,938 | 12/1995 | Jedesjo et al. | 436/135 |
| 5,516,489 | 5/1996 | Melgaard et al. | 436/135 |

FOREIGN PATENT DOCUMENTS

| | | |
|---|---|---|
| 560324 | 9/1993 | European Pat. Off. . |
| 560324A1 | 9/1993 | European Pat. Off. . |

OTHER PUBLICATIONS

Hord et al. "The Role of Hydrogen Peroxide in the SC2 Clean" Institute of Environmental Sciences, 1994 Proceedings vol. 1 40th Annual Technical Meeting.

Schmidt et al. "The Importance of $H_2O_2$ decomposition in Silicon Surface Cleaning". The Japan Society of Applied Physics, 419–421 Yohohama, 1994.

Ganapathisubramanian et al. "Oscillary Oxygen Evolution During Catalyzed Disproportionation of Hydrogen Peroxide". Journal of Physical Chemistry, vol. 85. 9, 1981, pp. 1103–1105.

Schmidt et al. "Physico Chemical Aspects of Hydrogen Peroxide Based Silicon Wafer Cleaning Solutions".

Schmidt, et al., "Physico Chemical Aspects of Hydrogen Peroxide Based Silicon Wafer Cleaning Solutions," Sep., 1994.

Hurd, et al., "The Role of Hydrogen Peroxide in the SC2 Clean", *Institute of Environmental Sciences*, 40th Annual Technical Meeting, Chicago, Illinois, May 1994.

Schmidt, et al., "The Importance of $H_2O_2$ Decomposition in Silicon Surface Cleaning", 1994 International Conference on Solid State Devices and Materials, Pacifico Yokohama, Yokohama, Japan, Aug. 1994.

*Primary Examiner*—Jill Warden
*Assistant Examiner*—Sharidan Carrillo
*Attorney, Agent, or Firm*—Knobbe, Martens, Olson & Bear LLP

[57] ABSTRACT

A method for evaluating, monitoring or controlling the efficiency, stability or exhaustion of a complexing or chelating agent present in a chemical solution used for oxidizing, dissolving, etching or stripping a semiconductor wafer wherein:

a chemical solution containing hydrogen peroxide as well as a complexing or chelating agent for contaminants present in the solution is used for oxidation, dissolution, etching or stripping a semiconductor wafer surface;

a measurement of the hydrogen peroxide decomposition is performed in situ in the solution;

the measurement of the $H_2O_2$ decomposition is used to provide information concerning the behavior of the complexing or chelating agent.

12 Claims, 6 Drawing Sheets

METHOD FOR EVALUATING, MONITORING OR CONTROLLING THE EFFICIENCY, STABILITY, OR EXHAUSTION OF A COMPLEXING OR CHELATING AGENT PRESENT IN A CHEMICAL SOLUTION USED FOR OXIDIZING, DISSOLVING, ETCHING OR STRIPPING A SEMICONDUCTOR WAFER

FIELD OF THE INVENTION

The present invention is related to a method for providing information about the behaviour of a complexing or chelating agent present in a chemical solution used for the oxidation, dissolution, etching or stripping of a semiconductor wafer.

More particularly, the present invention is related to an industrial method for evaluating, monitoring, or controlling the efficiency, stability, or exhaustion of such a chemical complexing or chelating agent.

BACKGROUND OF THE INVENTION

At the present time, the semiconductor industry is using notoriously unstable chemical mixtures for oxidizing, dissolving, etching and stripping semiconductor wafers. These mixtures can be defined generally as cleaning solutions.

Cleaning solutions are usually composed of hydrogen peroxide ($H_2O_2$) mixed with ammonium hydroxide (SC1 or APN mixture) or hydrochloric acid (SC2 or HPM mixture). Alternatively, cleaning solutions can be made up of $H_2O_2$ mixed with sulfuric acid (SPM mixture) or hydrofluoric acid (HF mixture).

The instability of such solutions is mainly caused by contaminants present in the cleaning bath, which are acting as catalysts for the decomposition of hydrogen peroxide. Usually such contaminants are metals or also $Br^-$ or $Cl^-$ anions. These impurities, and in particular metal contaminants, are also causing an additional problem by adsorbing onto the silicon wafer surface depending on the pH of the solution and on the surface conditions.

There are several approaches to reduce the adsorption of impurities on silicon surfaces using cleaning mixtures, for instance by adding a complexant or chelating agent to the bath.

Document DE-A-3822350 suggests adding ethylenediaminetetraacetic acid (EDTA) to cleaning solutions as a complexing agent. Documents EP-A-0560324 and U.S. Pat. No. 5,302,311 suggest using phosphonic acid based organic molecules as complexing agents. Although it is known that the addition of such agents provides a reduction in the surface metal pollution level, nothing is known about the stability of such complexing agents in the above-mentioned chemical mixtures. Furthermore, once the complexing agent is destroyed through the oxidizing power of the solution, contaminants (i.e., metals) will adsorb onto the wafer surface resulting in the degradation of devices built up on such surfaces.

Accordingly, it would be very useful to know the endpoint of the stability of the complexant, i.e. when the complexant is not effective anymore.

A conference presentation made by H. F. Schmidt et al. on September 1994 in Brugge (Belgium) concerning "Physico chemical aspects of hydrogen peroxide based silicon wafer cleaning solutions" reported on important aspects of hydrogen peroxide based chemical mixtures used to clean up silicon surfaces before they enter the device fabrication process and also after nearly each further processing step. Nothing is stated in this conference, however, concerning the behaviour of complexing agents.

SUMMARY OF THE INVENTION

The present invention aims to provide useful information on the behaviour of a complexing or chelating agent in chemical mixtures used for oxidation, dissolution, etching or stripping of semiconductor surfaces.

The present invention also aims to provide useful information about the efficiency or stability or exhaustion or lifetime of such agents and/or about the contaminant deposition level on the surface of a semiconductor.

More particularly, the present invention aims to provide an industrial method which will give such information in real time.

The present invention also aims to determine the optimum conditions for using the complexing or chelating agent in a corresponding cleaning or etching or stripping solution.

In one aspect, the present invention comprises a method for evaluating the metal complexing capacity of a complexing or chelating agent in $H_2O_2$-containing solutions that are employed in the treatment or processing of semiconductor surfaces. This method includes steps for monitoring the rate of decomposition or the change in concentration of the $H_2O_2$ in the solution; detecting a variation in the rate of decomposition or the change in concentration; and using this variation as an indicator of the exhaustion or saturation of the complexing or chelating agent. The $H_2O_2$ concentration can be monitored by measuring the decomposition of $H_2O_2$. The decomposition of $H_2O_2$ can, in turn, be monitored by measuring an increasing volume of $O_2$ at a constant pressure, or alternatively by measuring an increasing partial pressure of $O_2$ at a constant gas volume. According to one embodiment, the decomposition of $H_2O_2$ is monitored by measuring the flow rate of $O_2$ gas prime out of a system with fixed volume at constant pressure. According to another embodiment, the $H_2O_2$ concentration is monitored by a titration assay that can be a photometric titration assay. In yet another embodiment, the rate of decomposition of $H_2O_2$ is monitored by measuring the conductivity of the solution. An ion selective electrode can be used for this purpose. According to yet another embodiment, the monitoring step of the invented method provides real time information. The invented method can additionally include a step for separating the semiconductor material from the solution after detecting the variation in the rate of $H_2O_2$ decomposition. Further, the invented method can include a step that involves refreshing the solution after detecting the variation in the rate of $H_2O_2$ decomposition.

Another aspect of the invention comprises a method for processing a semiconductor material. This method involves steps for contacting a semiconductor material with an $H_2O_2$-containing solution; monitoring the rate of decomposition or the change in concentration of the $H_2O_2$ in the solution; detecting a variation in the rate of decomposition or the change in concentration; and separating the semiconductor material from the chemical solution when the variation is detected. The semiconductor material can be a semiconductor wafer which can be made from silicon.

A further aspect of the invention also comprises a method for processing a semiconductor material. The invented method includes steps for contacting a semiconductor material with an $H_2O_2$-containing solution; monitoring the rate of decomposition or the change in concentration of the $H_2O_2$ in the solution; detecting a variation in the rate of decomposition or the change in concentration; and adding a chelating agent, a metal complexing agent, or $H_2O_2$ to the solution when the variation is detected. According to one embodiment, the semiconductor material is a semiconductor wafer. This semiconductor wafer can be made from silicon.

DETAILED DESCRIPTION OF THE INVENTION

The present invention is related to a method for evaluating, monitoring or controlling the efficiency, stability, or exhaustion of a complexing or chelating agent present in a chemical solution used for the oxidation, dissolution, etching or stripping of a semiconductor wafer wherein:

- a solution containing hydrogen peroxide as well as a complexing or chelating agent for contaminants present in the solution is used for oxidation, dissolution, etching or stripping a semiconductor wafer;
- a measurement of the decomposition of the hydrogen peroxide is performed in situ in the chemical solution;
- such measurement of the $H_2O_2$ decomposition is used to provide information on the behaviour of the complexing or chelating agent present in the solution.

By in situ, it should be understood that the measurements are performed in the chemical solution or just above the chemical solution.

According to a preferred embodiment, such information will be used to evaluate, monitor or control the contaminant deposition level on the semiconductor wafer surface.

According to another preferred embodiment, such information will be used to determine the endpoint of the complexing or chelating agent.

Accordingly, such method of evaluation will be used either by suppliers of chemical agents (they will have full information about the efficiency and the stability of their products) or by semiconductor companies using such complexing or chelating agent in oxidation, dissolution, etching or stripping processes.

This means that in the case of a use by suppliers of a chemical agent, the method of the present invention is able to determine the optimum condition for using the complexing or chelating agent.

In the case of semiconductor companies, the method according to the present invention can be used in order to determine the moment when an oxidation, dissolution, etching or stripping process should be stopped.

Actually, the contaminants which are metal or $Br^-$ or $Cl^-$ impurities are catalyzing the decomposition reaction of $H_2O_2$ in a cleaning or etching or stripping solution. This means that when the impurities are complexed by chelating agents, they are not acting as decomposition catalysts so that the hydrogen peroxide shows higher stability. As soon as the complexing or chelating agent is destroyed, the contaminants come back into the catalysis cycle and the hydrogen peroxide shows lower stability.

Any measurement technique which is able to determine the $H_2O_2$ decomposition in a chemical solution can be used in the present invention.

Therefore, to measure such decomposition reaction of hydrogen peroxide in a cleaning solution, one can measure, for instance:

1° the produced $O_2$ volume at essentially constant pressure,

2° the $O_2$ pressure at constant volume.

According to another preferred embodiment, the measure of the hydrogen peroxide decomposition can be performed by titration. Photometric measurement can also be performed. For instance, this can be achieved by means of light absorption (IR, UV, etc.) in said solution and will give information on the concentration of the hydrogen peroxide. Any other methods such as the measurement of the conductivity of the solution can also be used.

Advantageously, such indirect methods of evaluation will be performed in situ during the cleaning process of semiconductor surfaces. This will give real time information and will not interfere with the corresponding process. Further information regarding in situ evaluations of semiconductor cleaning processes is contained in a co-pending U.S. patent application entitled "Electrochemical Measurements for In-situ Monitoring of Semiconductor Wafer Cleaning Processes," filed Feb. 3, 1995.

It should also be noted that this method of evaluation is efficient, precise and cheap.

Figure 1:
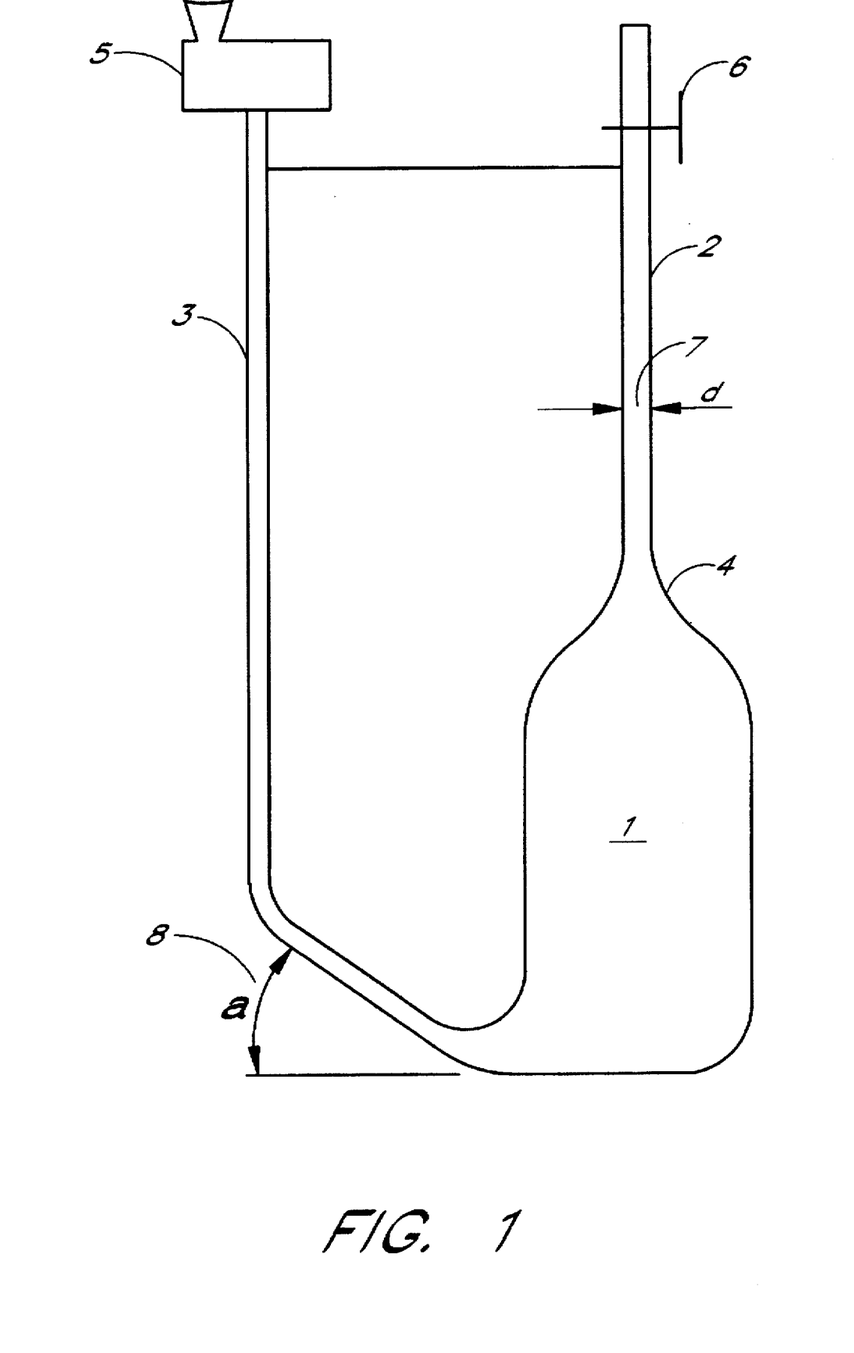
FIGS. 1, 2 and 3 show schematic views of devices used to determine the decomposition behaviour of $H_2O_2$.
Figure 2:
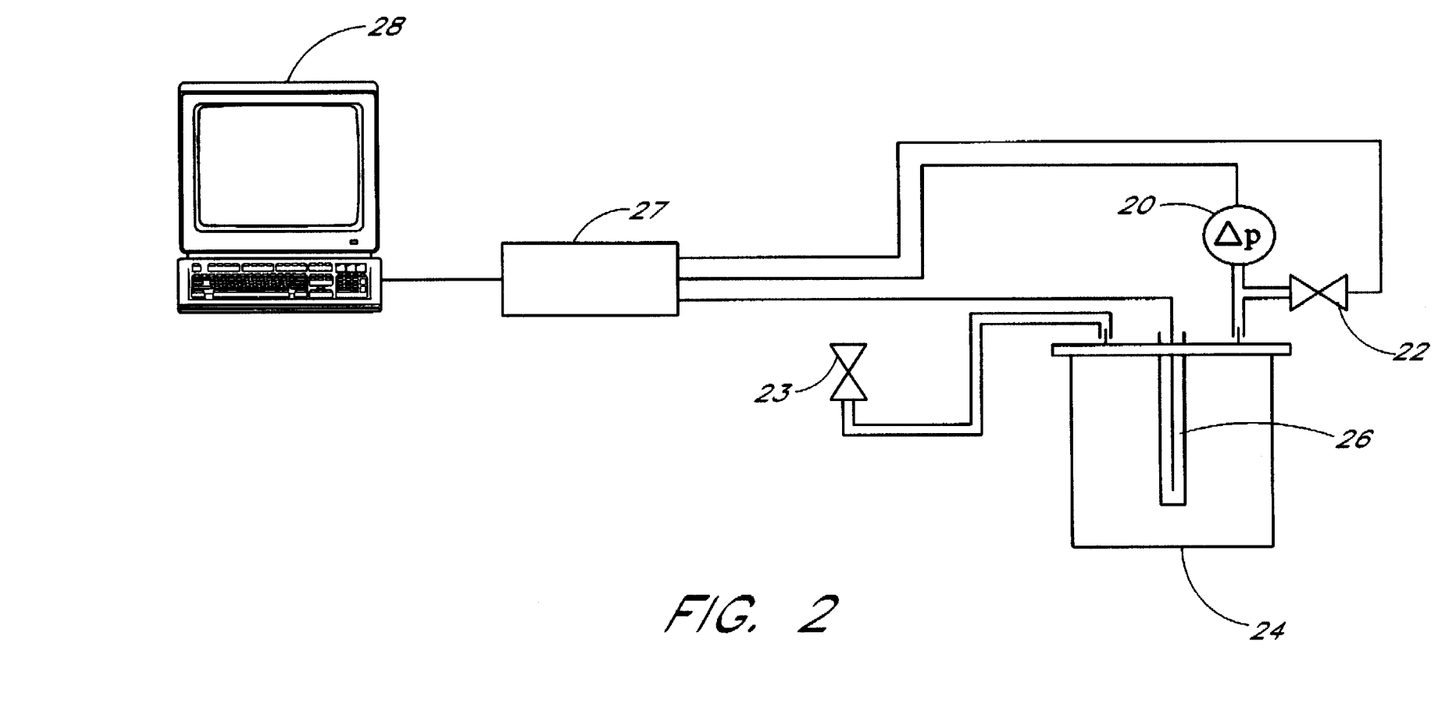
Figure 3:
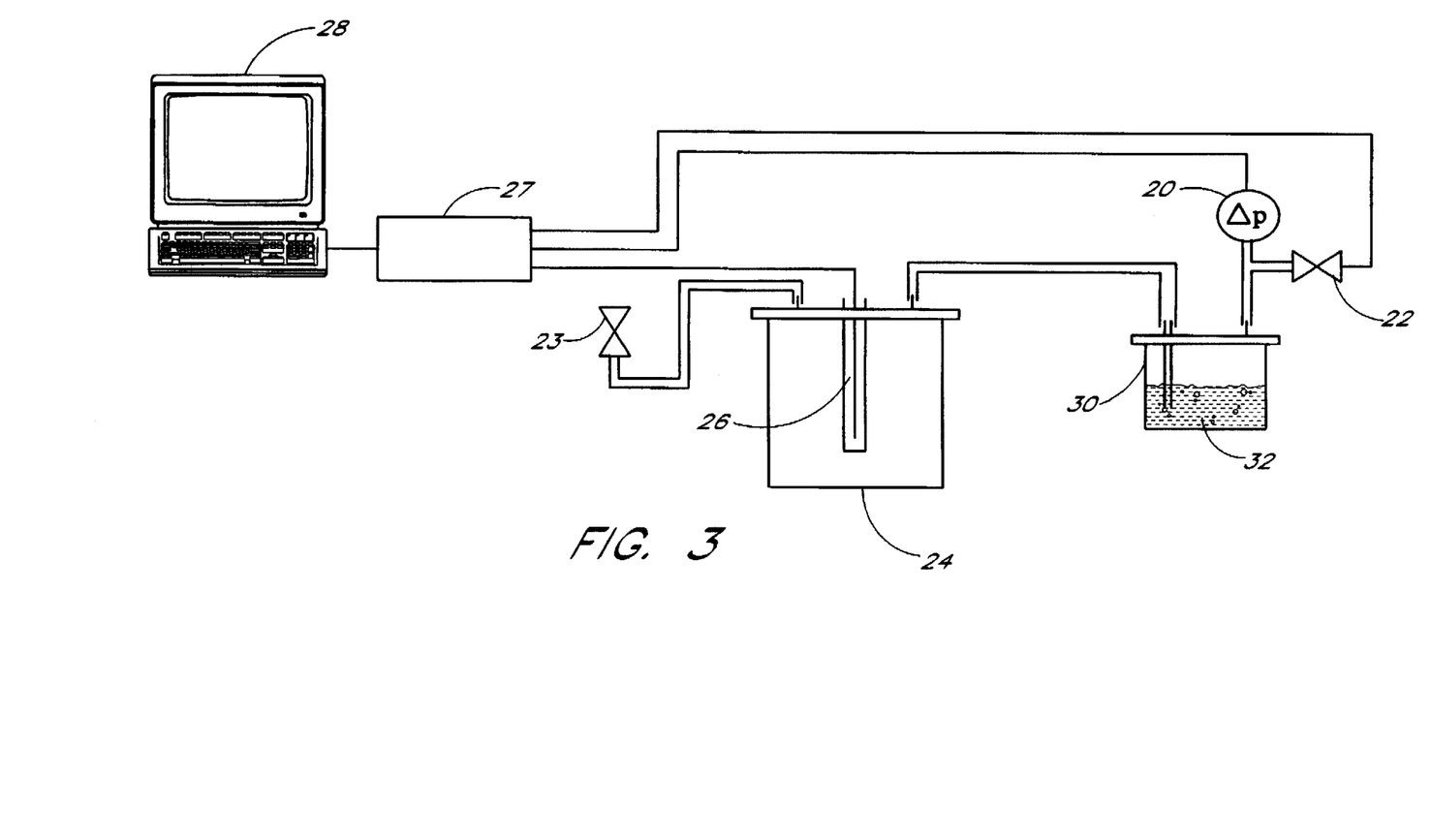

To determine the decomposition behaviour of $H_2O_2$ in real time, a gasometric technique is preferably used. FIG. 1, 2 and 3 show schematic views of several devices which have been developed by the applicants.

Several embodiments are hereunder proposed to determine the decomposition of $H_2O_2$ 1°) to measure the increasing $O_2$ volume at quasi constant pressure with a device as described in FIG. 1;

2°) to measure the increasing partial pressure of $O_2$ at constant gas volume with a decomposition method as described in FIG. 2;

3°) to measure the flow rate of $O_2$ gas stream of a system with a fixed volume and at a constant pressure.

FIG. 1 describes a U-tube made of made of quartz and comprising the reaction chamber for decomposition of $H_2O_2$. It has a fixed total volume and for accurate measurements it is very important to know:

(a) the volume of the "reaction chamber", (b) the inner diameter of the measuring part and (c) the length of the measuring part with great accuracy.

The "reaction chamber" 1 is that part of the U-tube in which the $H_2O_2$ decomposition occurs and which produces the gas built up in the measuring part 2. In one embodiment, the total volume of the reaction chamber is 57.0 ml with the inner diameter of the measuring part 7 being 5.55 mm in length, and the angle 8, formed by the elongated configuration of the non measuring part 3, is 35°.

The open side of the U-tube is called the "non measuring" part where the "storage chamber" 5 is built extra large and at the same height as the valve 6 on the measuring side. The change-over 4 from the reaction chamber 1 to the measuring part 2 is conical in shape. This design keeps the error caused by pressure differences between the measuring part and non measuring part minimum, because when the level of the liquid on the measuring side decreases by pressure built up under the valve, the liquid level on the open non measuring side is forced to increase. The time for a certain decrease in the solution level is measured manually or automatically. Then the valve is opened and the level of the test liquid is brought up again to the initial level. After closing the valve, further measurements are carried out. The gas evolution rate is the total volume of gas which is released out of a cleaning or etching or stripping solution, per unit time. Total volume of gas means the $O_2$ which is produced during the decomposition reaction and evaporated $NH_3$ and $H_2O$, which is a very small amount, because of the much lower vapour pressures compared to $O_2$. The decomposition rate is defined as the volume of $O_2$ per unit of time coming from the decomposition reaction of only pure $H_2O_2$. This technique is time consuming and it is unable to measure very fast or very slow decomposing $H_2O_2$.

In order to make the measurements more accurate and less time consuming an automated device has been developed as represented on FIG. 2. The liberation of $O_2$ causes a time-dependent increase of the pressure in a closed vessel with well-known volumes of the liquid and the gas phase. This pressure increase is monitored with a pressure sensor 20 (Hartman & Braun) of high sensitivity as a function of time. Because of the influence of the pressure on the reaction kinetics, the relationship between Δp and the time is only linear in a certain range, close to the atmospheric pressure. Therefore, at a certain selected pressure a valve 22 is used to release the gas and closes again at atmospheric pressure or at a preselected other pressure. A safety valve 23 also can be added. The temperature of the solution in the decomposition reactor 24 is measured by a thermocouple 26 which is a Digital Bench Temperature Indicator (thermo electric). An interface 27 is inserted between the measuring device and a computer 28. The computer program used to track pressure changes is controlled by a LAB-NB card in combination with Labview (Nat. instr). A PC samples the pressure and temperature as a function of time. For each of these measurements the decomposition rate is calculated from the slope of the pressure versus time plot and the volume of the gas which is a fixed value.

Using the tool shown in FIG. 2, the calculated decomposition rate is only correct if pure hydrogen peroxide solutions are tested at room temperature and with a linear pressure versus time response. Both the pressure and the volume are temperature dependent and therefore measurements at higher temperatures need to be corrected with a temperature related correction factor or the gas should be cooled down to room temperature. Another problem appears by mixing $H_2O_2$ with other chemicals like $NH_4OH$. In this case the build up of pressure is not only due to $O_2$ alone but also due to the evaporation of $N_3$ and $H_2O$ (which is pretty low, because of the vapour pressure difference between $O_2$, $NH_3$ and $H_2O$.)

These problems are mainly solved by extending the measurement setup by a second vessel 30 as represented on FIG. 3 where the gas is bubbled through another liquid 32 at room temperature to filter out the $NH_3$ and $H_2O$ vapours and to cool down the gas to room temperature. With fixed volumes of the two vessels, the accuracy and the sensitivity of the measurements can be optimized by changing the liquid volumes of the reaction mixture and the filtration medium.

Figure 4:
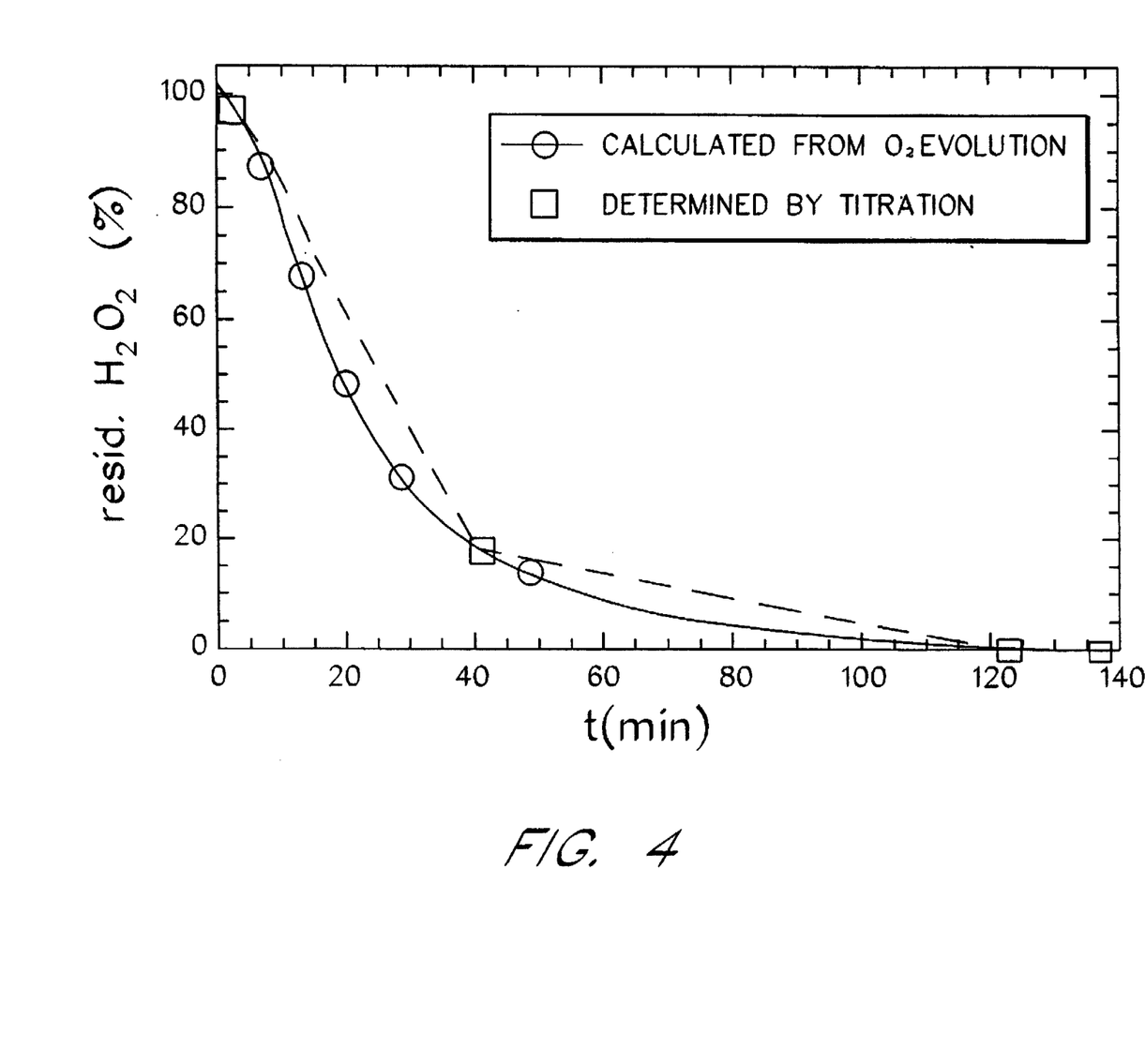
FIG. 4 represents the correlation between gasometric and titration techniques to determine the decomposition rate of $H_2O_2$ in a SC2 mixture.
Figure 5:
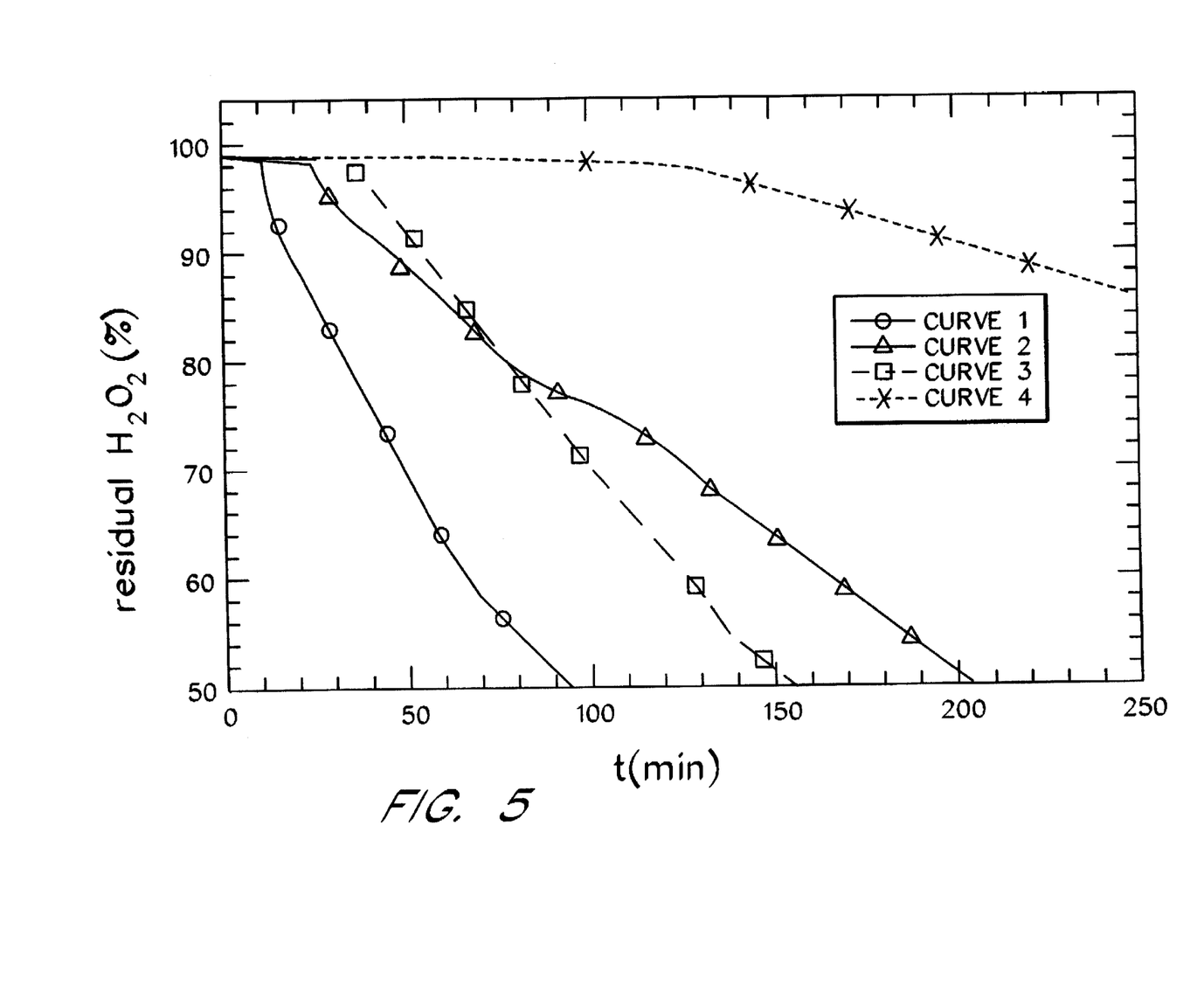
FIG. 5 represents the residual percentage of hydrogen peroxide in function of the time in a chemical solution as described hereunder in examples 1, 2, 3 & 4.

FIG. 4 represents an accuracy of the measurement method performed with the device as described in FIG. 5, cross-checked by titrametric analysis.

The present invention will be more particularly described for chemical solutions called SC1 mixtures used for cleaning semiconductor wafers and for which we have represented in FIG. 5 the decomposition of the hydrogen peroxide in function of the time.

In FIG. 5, the oxygen evolution rate for the following examples is measured by monitoring the pressure increase above the solution in function of the time (measured with the device represented in FIG. 3) and the residual $H_2O_2$ concentration is calculated from said information.

EXAMPLE 1

A solution (70° C.) of high purity ammonium hydroxide (NH4OH, 30% by weight), high purity hydrogen peroxide ($H_2O_2$, 30% by weight) and ultra pure water was contaminated with 1 ppb of iron and 1 ppb of Cu (both are known as good catalysts for the decomposition of $H_2O_2$ in such a solution).

Then the oxygen evolution rate, through the decomposition reaction of $H_2O_2$ was measured over several hours.
Result
As can be seen from curve 1 of FIG. 5, the $H_2O_2$ concentration decreases very fast after 10 min initiation time of the decomposition reaction. After already 90 min, the $H_2O_2$ concentration has decreased by 50%.

EXAMPLE 2

To the above mentioned solution described in example 1, 1 ppm of EDTA has been added together with the metal contaminants.
Result
As can be seen from curve 2 of FIG. 5, the $H_2O_2$ concentration stays pretty constant over around 25 minutes. After this time the concentration decreases very fast which means that the complexant (EDTA) has been destroyed and is not effective anymore. Wafers which are immersed 25 minutes in such solution show higher metal contamination.

EXAMPLE 3

To the above mentioned solution described in example 1, 1000 ppm of EDTA have been added together with the metal contaminants.
Result
As can be seen from curve 3 of FIG. 5, the $H_2O_2$ concentration stays pretty constant over around 40 minutes. After this time the concentration decreases very fast which means that the complexant (EDTA) has been destroyed and is not effective anymore.

EXAMPLE 4

To the above mentioned solution described in example 1, 1 ppm of EDTA has been added together with the metal contaminants and the temperature has been lowered from 70 to 50° C.
Result
As can be seen from curve 4 of FIG.5, the $H_2O_2$ concentration stays very constant over around 130 minutes. After this time the concentration decreases again very fast which means that the complexant (EDTA) has been destroyed and is not effective anymore.

Accordingly, one can summarize the situation as follows:
When an $H_2O_2$ containing mixture is contaminated with metallic impurities, the $H_2O_2$ becomes very unstable and decomposes to water ($H_2O$) and oxygen ($O_2$). This means that the solution loses over time its activity as a silicon surface cleaning solution.

For instance, 50% of the $H_2O_2$ decomposes within 90 minutes, when 1 ppb Fe and 1 ppb Cu (as nitrates) are added to the mixtures described in FIG. 5.

By adding, e.g., 1 ppm of a complexing agent (e.g. ethylenediaminetetraacetic acid=EDTA) the metals become complexed and are not active as catalysts anymore. This results in a stabilization of the $H_2O_2$ in the chemical cleaning solution. Nevertheless after a certain time, the complexant will loose its efficiency and the metals become free again and can act as decomposition catalysts. In the case as illustrated, the $H_2O_2$ concentration stays very constant over a certain time (i.e. around 40 min.—see FIG. 1) and decomposes very fast after a certain point, where the complexant has been finally destroyed through the oxidizing power solution.

It is now very important to understand the factors which are influencing the behaviour or stability (=lifetime) of such complexant to determine how long a certain stabilized cleaning solution can be used and, as a very important factor, which additives (which is the complexing/chelating agent) give the best performance.

Figure 6:
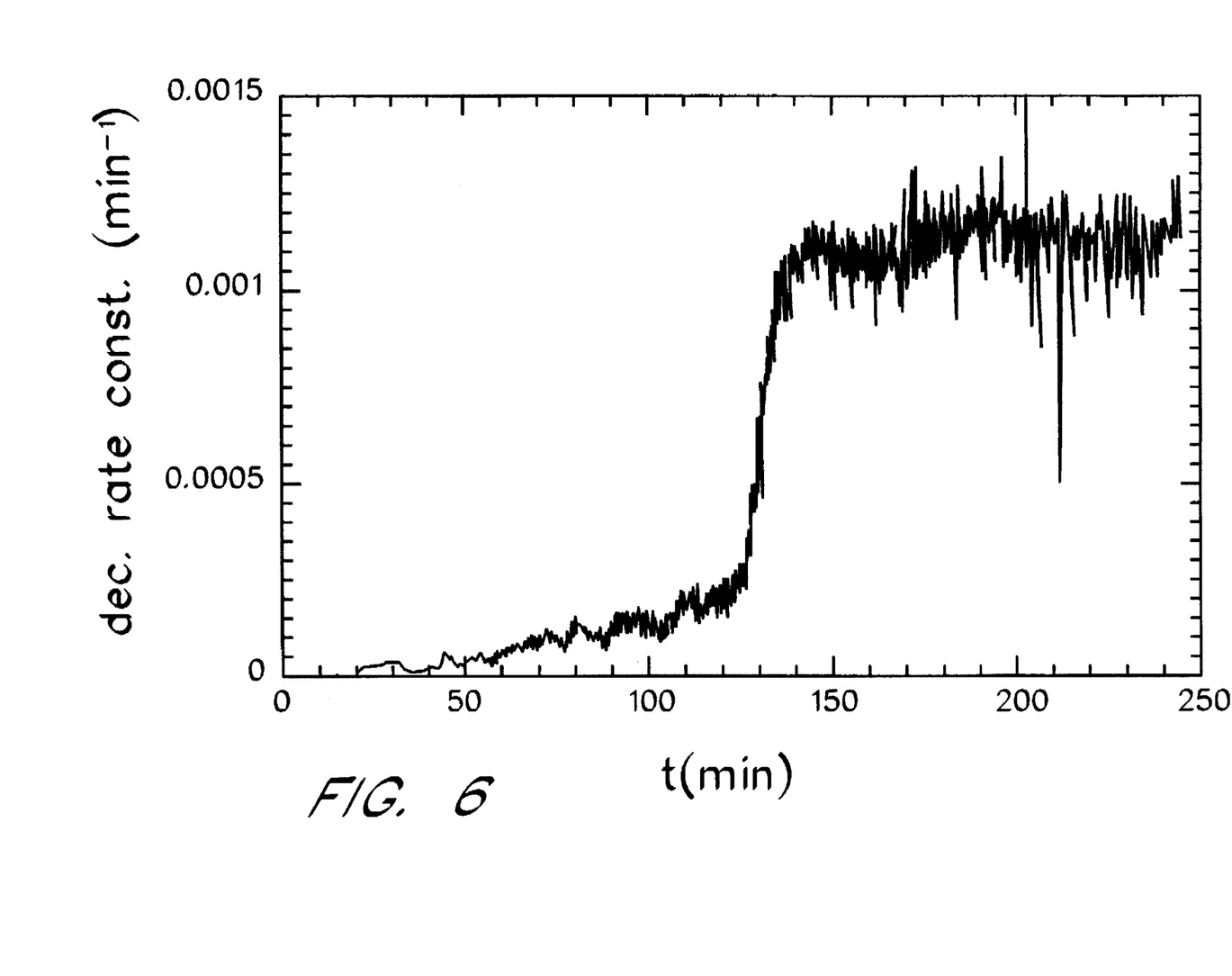
FIG. 6 represents the decomposition rate constant of $H_2O_2$ graph which can be used for determining the endpoint of a complexant lifetime.

FIG. 6 which represents the decomposition rate constant graph is also able to provide information the stability of a complexing agent and more particularly able to determine the endpoint of a complexant lifetime.

We can define the endpoint as the moment (taking into account the safety span) where the decomposition rate (the instability of $H_2O_2$) increases suddenly and which is the time when the metal ions become free again from the complexant. The endpoint of the reaction depicted in FIG. 6 will be represented by a peak if the derivative is taken of the curve shown in FIG. 6.

Any other methods which will give information concerning the hydrogen peroxide decomposition in a solution such as titration, photometric measurements, and conductivity measurements can be used in order to evaluate the efficiency of the metal complexing capacity of a complexing agent used in a cleaning solution for semiconductor surfaces.

As already mentioned, such information can be used as an example by suppliers of chemical agents in order to have information concerning their products or by semiconductor companies in order to determine the moment for which the oxidation, dissolution, etching or stripping process should be stopped.

It is clear that the above-described embodiment is but one example of a suitable arrangement for carrying out the invention. While the invention has been described in a few detailed examples it is evident that many alternatives will be apparent in the light of the foregoing description to those skilled in the art, the spirit and scope of the present invention being limited only by the terms of the appended claims. In addition, all documents, patent applications, and other references mentioned herein are hereby incorporated by reference.

What we claim is:

1. A method for evaluating exhaustion of a complexing or chelating agent in a solution, comprising $H_2O_2$ molecules and said complexing or chelating agent said method comprising the steps of:

a. monitoring a rate of decomposition of said $H_2O_2$ molecules in said solution;

b. detecting a change in the rate of said decomposition of said $H_2O_2$ molecules in said solution, and c. correlating said change in the rate of decomposition of said $H_2O_2$ molecules to the exhaustion of said complexing or chelating agent present in said solution.

2. A method according to claim 1, wherein said rate of decomposition of said $H_2O_2$ molecules is monitored by measuring an increasing volume of $O_2$ at a constant pressure.

3. A method according to claim 1 wherein said rate of decomposition of said $H_2O_2$ molecules is monitored by measuring an increasing partial pressure of $O_2$ at a constant gas volume.

4. A method according to claim 1, wherein said rate of decomposition of said $H_2O_2$ molecules is monitored by measuring a flow rate of an $O_2$ gas stream with a fixed volume at a constant pressure.

5. A method according to claim 1, wherein said rate of decomposition is monitored by a titration assay.

6. A method according to claim 5, wherein the titration assay includes a photometric measurement.

7. A method according to claim 1, wherein the rate of said decomposition of said $H_2O_2$ molecules is monitored by measuring conductivity of said solution.

8. A method according to claim 7, wherein said solution is measured with an ion selective electrode.

9. The method of claim 1, further comprising the step of immersing a semiconductor substrate in said solution and removing said substrate after detecting the rate of decomposition of said $H_2O_2$ molecules.

10. The method of claim 8, wherein said solution is a first solution, and further comprising the step of immersing a substrate in a second solution comprising $H_2O_2$ molecules and a complexing or chelating agent after detecting the rate of decomposition of said $H_2O_2$ molecules in said solution.

11. A method for evaluating saturation of a complexing or chelating agent in a solution comprising $H_2O_2$ molecules and said complexing or chelating agent, said method comprising the steps of:

a. monitoring a rate of decomposition of said $H_2O_2$ molecules in said solution;

b. detecting a change in the rate of said decomposition of said $H_2O_2$ molecules in said solution, and c. correlating said change in the rate of decomposition of said $H_2O_2$ molecules to the saturation of said complexing or chelating agent present in said solution.

12. A method for evaluating stability of a complexing or chelating agent in a solution comprising $H_2O_2$ molecules and said complexing or chelating agent, said method comprising the steps of:

a. monitoring a rate of decomposition of said $H_2O_2$ molecules in said solution;

b. detecting a change in the rate of said decomposition of said $H_2O_2$ molecules in said solution, and c. correlating said change in the rate of decomposition of said $H_2O_2$ molecules to the stability of said complexing or chelating agent present in said solution.

* * * * *

UNITED STATES PATENT AND TRADEMARK OFFICE
CERTIFICATE OF CORRECTION

PATENT NO. : 5,712,168  
APPLICATION NO. : 08/384272  
DATED : January 27, 1998  
INVENTOR(S) : Schmidt et al.

Page 1 of 2

It is certified that error appears in the above-identified patent and that said Letters Patent is hereby corrected as shown below:

On Title Page Item (73), under Assignee, line 1, after "IMEC", insert -- Kapeldreef 75, B–3001 --.

Title Page Item (21), under Appl. No., line 1, delete "384,272", insert -- 08/384,272 --, therefor.

Title Page Item (56), under U.S. Patent Documents, line 1, after "2,617,940", insert -- * --.

Title Page Item (56), under U.S. Patent Documents, line 2, after "5,081,045", insert -- * --.

Title Page Item (56), under U.S. Patent Documents, line 3, after "5,100,624", insert -- * --.

Title Page Item (56), under U.S. Patent Documents, line 4, after "5,290,361", insert -- * --.

Title Page Item (56), under U.S. Patent Documents, line 5, after "5,302,311", insert -- * --.

Title Page Item (56), under U.S. Patent Documents, line 6, after "5,438,002", insert -- * --.

Title Page Item (56), under U.S. Patent Documents, line 7, after "5,474, 938", insert -- * --.

Title Page Item (56), under U.S. Patent Documents, line 8, after "5,516,489", insert -- * --.

Title Page Item (56), under Foreign Patent Documents, line 1, after "560324", insert -- * --.

Title Page Item (57), under Abstract, line 14, delete "behavior" and insert -- behaviour --, therefor.

In Column 1, line 37 (Approx.), delete "$\overline{\overline{Ci}}$" and insert -- $\overline{\overline{CI}}$ --, therefor.

In Column 3, line 62, delete "$\overline{\overline{Ci}}$" and insert -- $\overline{\overline{CI}}$ --, therefor.

In Column 4, line 32 (Approx.), delete "FIG." and insert -- FIGS. --, therefor.

UNITED STATES PATENT AND TRADEMARK OFFICE
CERTIFICATE OF CORRECTION

PATENT NO. : 5,712,168
APPLICATION NO. : 08/384272
DATED : January 27, 1998
INVENTOR(S) : Schmidt et al.

It is certified that error appears in the above-identified patent and that said Letters Patent is hereby corrected as shown below:

In Column 4, line 36 (Approx.), after "$H_2O_2$", insert -- : --.

In Column 5, line 50, delete "$N_3$" and insert -- $NH_3$ --, therefor.

In Column 5, line 52, after "$H_2O$.)", insert -- . --.

In Column 6, line 11 (Approx.), delete "(NH4OH," and insert -- ($NH_4OH$, --, therefor.

In Column 6, line 60, delete "H2O2 containing" and insert -- $H_2O_2$ – containing -- therefor.

In Column 7, line 54, in Claim 1, delete "solution," and insert -- solution --, therefor.

In Column 7, line 55, in Claim 1, after "agent", insert -- , --.

In Column 7, line 60, in Claim 1, delete "solution," and insert -- solution; --, therefor.

In Column 8, line 8, in Claim 3, after "1" insert -- , --.

In Column 8, line 43, in Claim 11, delete "solution," and insert -- solution; --, therefor.

In Column 8, line 55, in Claim 12, delete "solution," and insert -- solution; --, therefor.

Signed and Sealed this

Thirtieth Day of January, 2007

JON W. DUDAS
*Director of the United States Patent and Trademark Office*